United States Patent [19]

Tanaka et al.

[11] Patent Number: 5,229,001
[45] Date of Patent: Jul. 20, 1993

[54] PROCESS FOR EXTRACTING INDOLES

[75] Inventors: Shin Tanaka; Akinori Matsuura, both of Chiba; Shintaro Furusaki, Fujisawa, all of Japan

[73] Assignee: Kawasaki Steel Corp., Hyogo, Japan

[21] Appl. No.: 689,454

[22] Filed: Apr. 22, 1991

[30] Foreign Application Priority Data

Apr. 27, 1990 [JP] Japan .................................. 2-114016

[51] Int. Cl.$^5$ ............................................. B01D 11/04
[52] U.S. Cl. ..................................... 210/634; 210/511
[58] Field of Search ....................... 210/634, 511; 544/7; 548/531; 430/580

[56]     References Cited
U.S. PATENT DOCUMENTS 4,025,347  5/1977  Beretta et al. ................... 430/580 X
4,585,472  4/1986  Hamprecht et al. ................. 544/7 X

FOREIGN PATENT DOCUMENTS 2061938  5/1981  United Kingdom .

OTHER PUBLICATIONS

European Search Report (2 pages).
Chemical Abstracts vol. 99, Nov. 28, 1983, No. 22.

Primary Examiner—Frank Spear
Attorney, Agent, or Firm—Bierman & Muserlian

[57]     ABSTRACT

The invention provides a process for the extraction of indoles which comprises the steps of firstly extracting indoles from an indoles containing mixture with formamide or a formamide-containing solution and subsequently contacting the extract with at least one organic solvent selected from the group consisting of ethers, aromatic hydrocarbons and halogenated hydrocarbons to recover indoles with the organic solvent. This process is applicable to an industrial scale extraction of indoles, because the extraction solvent system has a high extraction selectivity of indoles, is required in a small amount with almost no losses through the extraction and recovery steps and can be used repeatedly.

6 Claims, 2 Drawing Sheets

A flow diagram of the extraction process of indoles

Fig. 1 A flow diagram of the extraction process of indoles
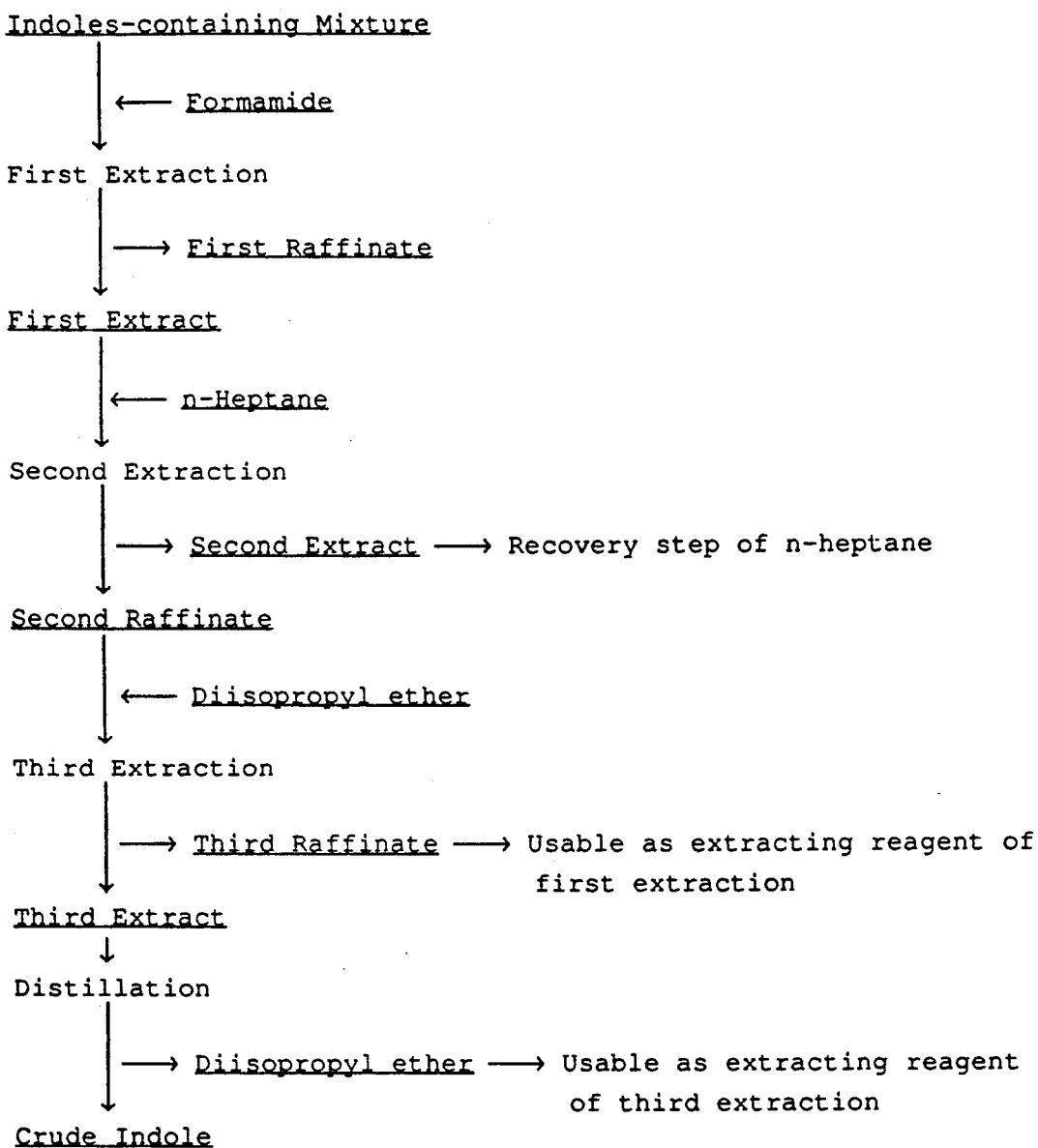

Fig. 2 A flow diagram of the extraction process of indoles
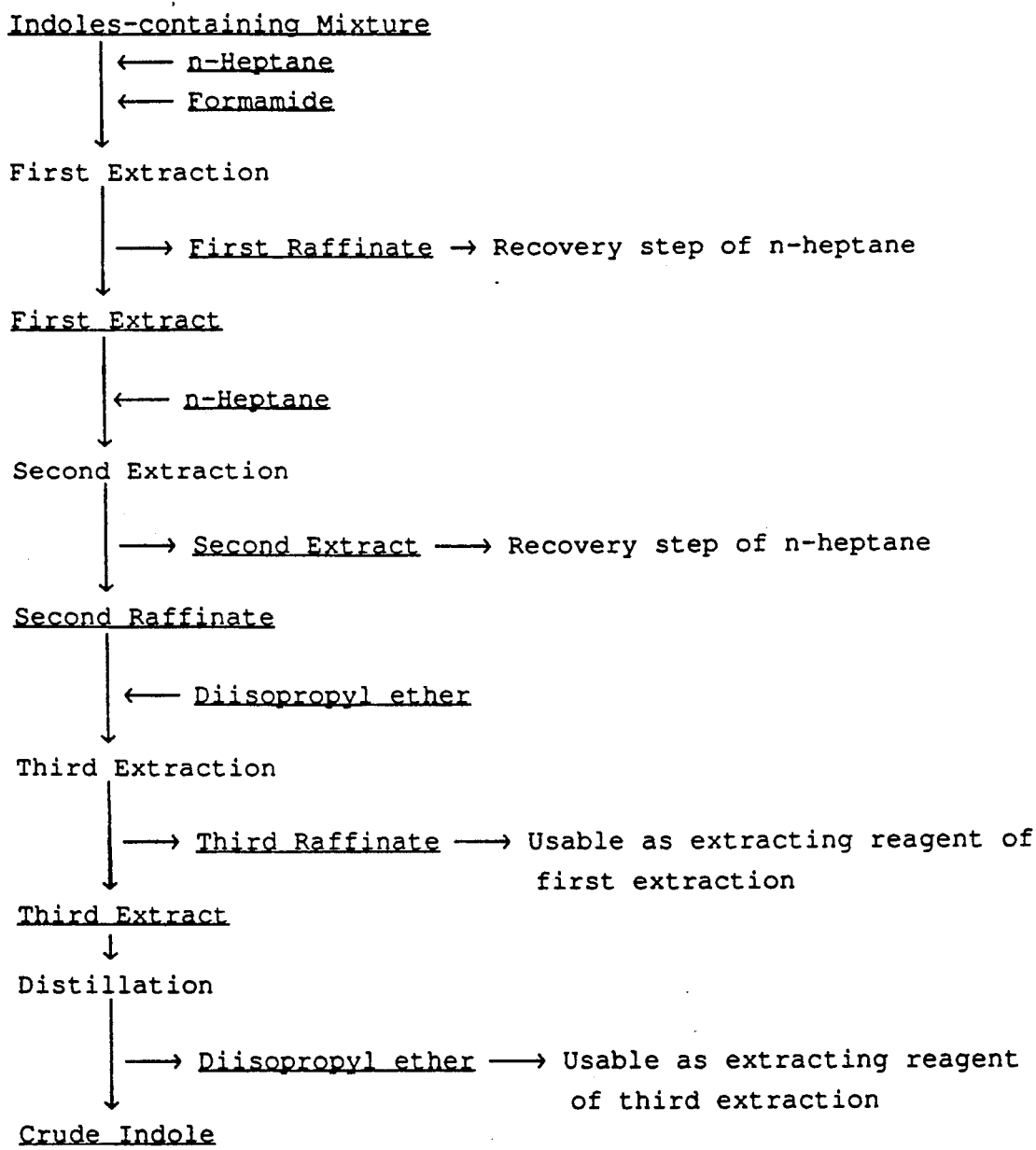

PROCESS FOR EXTRACTING INDOLES

FIELD OF THE INVENTION

This invention relates to a process for the extraction of indoles from a mixture of organic compounds containing indoles. Particularly, this invention relates to a process for the extraction of indoles from an indoles-containing mixture in which formamide or a formamide-containing solution is used as an extracting reagent.

BACKGROUND OF THE INVENTION

Indoles are expensive but important compounds for use in the preparation of perfumes and as materials for the synthesis of tryptophan, medicines, agricultural chemicals and the like.

Indoles are contained in coal tar, coal-liquefied oil and the like in relatively large quantities. A liquid-liquid extraction method has been proposed as an industrial scale process for the recovery of indoles from these indoles-containing mixtures. In this instance, glycols such as ethylene glycol and ethanolamines such as monoethanolamine have been reported as useful extracting reagents having a high extraction selectivity of indoles.

Since the extraction selectivity of indoles is not satisfactorily high even by the use of such extracting reagents, a process has been studied and proposed in which these extracting reagents are used jointly with aliphatic hydrocarbons such as heptane with the aim of increasing partition coefficient of indoles and, at the same time, decreasing partition coefficients of impurities. A purification process has also been proposed in which impurities in an indoles-containing extract are removed by the extraction with aliphatic hydrocarbons such as heptane.

The term "extraction selectivity is high" as used herein means that a compound of interest in an extraction system has a high partition coefficient compared to those of incidental impurities.

The following summarizes typical processes for the extraction of indoles proposed on the basis of aforementioned studies.

(1) An indole-containing mixture is contacted with an aliphatic hydrocarbon, such as n-heptane, and monoethanolamine to extract indole from the mixture into monoethanolamine layer. The resulting extract (monoethanolamine layer) is then subjected to a distillation step directly or after extracting and removing impurities from the extract by contacting it with an aliphatic hydrocarbon such as n-heptane. Thereafter, a monoethanolamine azeotropic fraction and an indole fraction are obtained by means of rectification. [Koks i Khimiya, 1981 (5), 37–41].

(2) Indole is extracted with ethylene glycol from a mixture containing indole by contacting the mixture with ethylene glycol. The resulting extract (ethylene glycol solution) is contacted with an aliphatic hydrocarbon such as n-heptane to extract impurities from the extract. After the removal of impurities, the resulting raffinate (ethylene glycol solution) is contacted with diisopropyl ether to extract indole with the ether. The resulting extract (diisopropyl ether solution) is subjected to distillation to distill off diisopropyl ether and then washed with water to remove ethylene glycol. Thereafter, an indole fraction is obtained by means of rectification. [U.S. Pat. No. 2,837,531 (1958)].

Each of the aforementioned prior art processes, however, has some disadvantages.

For example, since monoethanolamine has a low selectivity of indole extraction, large quantities of aliphatic hydrocarbons are inevitably used in the aforementioned process (1) in order to improve the extraction selectivity. Especially, large amounts of aliphatic hydrocarbons which exceed the amount of a feed oil as a starting material are required when indoles are extracted selectively from the feed containing a low level of indoles. In consequence, this process has a problem of requiring considerably high costs for the recovery of aliphatic hydrocarbons by distillation and for the installation of equipment.

In the case of the process (2), ethylene glycol for use in the extraction of indoles has a considerable mutual solubility with the other extraction solvent, diisopropyl ether. Consequently, not only the recovery yield of these solvents is low but also the process requires additional treatment steps for the removal of contaminated solvents and the like, thus resulting in the considerably high production cost. A disadvantage of this process is that ethylene glycol has an insufficient selectivity of indole extraction.

The indoles extracted by these processes (1) and (2) contain a significant amount of organic sulfuric compounds such as benzothiophenes, resulting in disadvantages as goods on the market. Therefore, it is necessary to apply additional and costly indole-purification processes.

This invention contemplates overcoming the foregoing problems involved in the prior art.

SUMMARY OF THE INVENTION

In view of the above, it therefore becomes an object of this invention to provide an industrial process for the extraction of indoles with a high extraction selectivity.

Particularly, in accordance with the present invention, there is provided a process for the extraction of indoles from an indoles-containing mixture which comprises using formamide or a formamide-containing solution as an extracting reagent. More particularly, there is provided a process for the extraction of indoles which comprises the steps of; (a) extracting indoles from an indoles-containing mixture with formamide or a formamide-containing solution, and (b) recovering indoles from the extract of step (a).

Also preferably, at least one organic solvent (A) selected from the group consisting of ethers, aromatic hydrocarbons and halogenated hydrocarbons is used for the recovery of indoles in the recovering step (b). Also preferably, the process for the extraction of indoles of the present invention further comprises a purification step interposed between the steps (a) and (b), wherein the purification step comprises extracting impurities from the extract resulting from the step (a) with at least one organic solvent (B) selected from the group consisting of aliphatic hydrocarbons and alicyclic hydrocarbons. Preferably, formamide or a formamide-containing solution for use in the extraction step (a) coexists with at least one organic solvent (B) selected from the group consisting of aliphatic hydrocarbons and alicyclic hydrocarbons.

Other objects and advantages of the present invention will be made apparent as the description progresses.

BRIEF DESCRIPTION OF THE DRAWINGS

FIG. 1 is a flow diagram showing an example of the process for the extraction of indoles of this invention.

FIG. 2 is a flow diagram showing another example of the process for the extraction of indoles of this invention.

DETAILED DESCRIPTION OF THE INVENTION

Indoles to be extracted by the process of the present invention include for instance indole, a substituted indole containing a substituent alkyl group such as methylindole. The term "indoles-containing mixture" as used herein is intended to include any mixture useful as the starting material of the present invention, provided that it contains at least indoles such as indole, methylindoles and the like, though it is preferable that the mixture be composed of indoles and hydrocarbons as the main components.

A typical example of such a starting material is an indoles-containing fraction having a boiling range of from 200° to 300° C. at atmospheric pressure, which is obtained from coal tar by distillation. Such a fraction contains indole and methylindoles as the source of indoles, naphthalene, methylnaphthalenes, dimethylnaphthalenes, diphenyl, acenaphthene, dibenzofuran, fluorene and the like as the source of hydrocarbons, and benzothiophenes, methyl-benzothiophenes, thienopyridines and the like as the source of organic sulfuric compounds.

This fraction further contains acidic components such as phenols and basic components such as quinolines. Prior to the use of this fraction as the starting material of the present invention, these components may preferably be removed by means of, for instance, extraction with an aqueous alkali solution and an aqueous acid solution.

Even in the coexistence of these acidic and basic components, this fraction can be used as the starting material of the present invention. In this instance, these acidic and basic components as contaminants may be removed from the finally recovered indoles, or preferably from indoles-containing extracts as intermediate products of the extraction process (ethers, aromatic hydrocarbons, halogenated hydrocarbons and the like containing indole), by washing out these impurities with an aqueous alkali solution and an aqueous acid solution.

The process of the present invention is characterized in that formamide or a formamide-containing solution, most preferably formamide, is used as an extracting reagent for the extraction of indoles.

The extraction step making use of formamide or a formamide-containing solution is not specifically limited and, therefore, usually used means such as liquid membrane process and the like may be applicable. However, the extraction step may preferably be completed by mixing formamide or a formamide-containing solution with a starting oil, stirring the mixture and then settling the stirred mixture to separate it into an extract layer and a raffinate layer.

Illustrative examples of the formamide-containing solution include aqueous solution of formamide and other solutions of formamide dissolved in solvents having compatibility with formamide such as glycols (ethylene glycols and the like), monoethanolamine and the like. Extraction selectivity of indoles may be improved by the use of aqueous solution of formamide because, compared to the case of formamide, aqueous solution of formamide has a markedly low capacity to dissolve hydrocarbons contained as impurities in an indoles-containing mixture.

The specific gravity of formamide is higher than those of ethylene glycol and monoethanolamine. As the results, an extract layer (formamide layer) and a raffinate layer (the starting material from which indoles have removed containing impurities such as hydrocarbons) may have significantly different specific gravities from each other and therefore show a high phase separation. In the case of a commonly used extraction process in which monoethanolamine is used as an extracting reagent, the difference in specific gravities between both layers, that is an extract layer (monoethanol layer) and a raffinate layer, is small and, therefore, phase separation of these layers is not so good, thus resulting in the mutual contamination of the two layers. The prior art extraction process has problems of causing significant loss in the recovery of the extracting reagent and of lowering the extraction selectivity of indoles.

Contrary to this, loss of formamide during the extraction process in this invention hardly occurs because of its low mutual solubility with hydrocarbons contained as impurities in the starting material.

Though not specifically limited, recovery of indoles from the thus obtained solution of indoles (extract) extracted with formamide or a formamide containing solution may for example be achieved by directly subjecting indoles in the extract to distillation or by subjecting the indoles firstly to back extraction with an appropriate solvent and then removing the solvent by means of distillation, evaporation or the like.

The following describes the just mentioned back extraction method for the recovery of indoles.

In this instance, a solvent which can be separated easily from indoles may be used preferably as the back extraction solvent. An illustrative example of such a preferred solvent may have different boiling point from those of indoles and may not form azeotropic mixture with indoles. By using such a solvent, loss in the recovery yield of indoles could be minimized.

Recovery of indoles from the extract obtained by the extraction of indoles with formamide or a formamide-containing solution may be contacted most preferably by extracting indoles to an extracting reagent comprises at least one organic solvent (A) selected from the group consisting of ethers, aromatic hydrocarbons and halogenated hydrocarbons. This back extraction method is preferred because it can reduce the losses of formamide and indoles having a low heat resistivity.

In addition to the organic solvent (A), nitrated hydrocarbons may also be useful for the back extraction of indoles, though the use of such hydrocarbons has a problem of requiring complex handling from a safety point of view.

Illustrative examples of ethers as the source of the organic solvent (A) include diethyl ether, diisopropyl ether, dipropyl ether, dibutyl ether, ethyl vinyl ether, butyl vinyl ether, anisole, phenetol, methoxytoluene, benzyl ethyl ether and the like.

Useful aromatic hydrocarbons include benzene, toluene, o-xylene, m-xylene, p-xylene, ethylbenzene, cumene, mesitylene, tetralin, n-butylbenzene, sec-butylbenzene, tert-butylbenzene, p-cymene, o-diethylbenzene, m-diethylbenzene, p-diethylbenzene, styrene and the like.

Useful halogenated hydrocarbons include dichloromethane, chloroform, carbon tetrachloride, 1,1-dichloroethane, 1,2-dichloroethane, 1,1,1-trichloroethane, 1,1,2-trichloroethane, 1,1,1,2-tetrachloroethane, 1,1,2,2-tetrachloroethane, pentachloroethane, hexachloroethane, 1,1-dichloroethylene, 1,2-dichloroethylene, trichloroethylene, tetrachloroethylene, propyl chloride, isopropyl chloride, 1,2-dichloropropane, 1,2,3-trichloropropane, allyl chloride, butyl chloride, sec-butyl chloride, isobutyl chloride, tert-butyl chloride, 1-chloropentane, chlorobenzene, o-dichlorobenzene, m-dichlorobenzene, p-dichlorobenzene, o-chlorotoluene, m-chlorotoluene, p-chlorotoluene, bromoform, ethyl bromide, 1,2-dibromoethane, propyl bromide, isopropyl bromide, bromobenzene, fluorobenzene, benzotrifluoride, hexafluorobenzene, chlorobromomethane, trichlorofluoromethane, 1-bromo-2-chloroethane, 1,1,2-trichlorofluoromethane, 1-bromo-2-chloroethane, 1,1,2-trichloro-1,2,2-trifluoroethane, 1,1,2,2-tetrachloro-1,2-difluoroethane and the like.

The thus recovered indoles by their extraction with an organic solvent (A) may be separated easily from the organic solvent (A), for example, by removing the solvent by means of distillation, evaporation or the like.

Since indoles thus separated from the organic solvent (A) may still contain a small amount of impurities, if necessary, the thus obtained indoles may be subjected to a purification step by employing a usually used means such as distillation, crystallization or the like.

According to the process of the present invention, as described in the foregoing, indoles may be recovered from the indoles-containing extract preferably by contacting the extract with an organic solvent (A) and extracting indoles with the solvent.

The indoles-containing extract may be contaminated sometimes with hydrocarbons as impurities originally contained in the starting oil, which will cause reduction of extraction selectivity of indoles. In such a case, the recovery of indoles by extraction may be carried out after removing these impurities from the extract.

Though separation of impurities may be effected by usually used means such as distillation, extraction, absorption, crystallization or the like, it is preferable to employ a method in which impurities contained in the extract are extracted and removed by contacting the extract with at least one organic solvent (B) selected from the group consisting of aliphatic hydrocarbons and alicyclic hydrocarbons from the viewpoint of easy handling and high impurities-removing efficiency.

Illustrative examples of aliphatic hydrocarbons for use in the extraction removal of impurities include n-pentane, 2-methylbutane, n-hexane, 2-methylpentane, 2,2-dimethylbutane, 2,3-dimethylbutane, n-heptane, 2-methylhexane, 3-methylhexane, 2,3-dimethylpentane, 2,4-dimethylpentane, n-octane, 2,2,3-trimethylpentane, 2,2,4-trimethylpentane, n-nonane, 2,2,5-trimethylhexane, n-decane, 1-pentene, 2-pentene, 1-hexene, 1-heptene, 1-octene, 1-nonene, 1-decene and the like.

Illustrative examples of useful alicyclic hydrocarbons include cyclopentane, methylcyclopentane, cyclohexane, methylcyclohexane, ethylcyclohexane, p-menthane, decalin, cyclohexene and the like.

Petroleum ether, petroleum benzine and the like may also be useful as mixed sources of these compounds.

In consequence, at least one compound may be selected from these compounds.

If necessary, indoles lost by their mixing in the impurities-extracted organic solvent (B) may be recovered for example by means of extraction with formamide or a formamide-containing solution.

The following describes a distillation method for the recovery of indoles from an indoles-containing solution (extract) extracted with formamide or a formamide-containing solution.

Formamide may be partially decomposed by heat when distillation is carried out at atmospheric pressure under a high temperature condition. Therefore, though recovery of indoles from the extract may be effected by distillation, it is necessary to prevent thermal decomposition of formamide by taking a countermeasure such as distillation under a reduced pressure. Distillation under a reduced pressure is preferable also from a viewpoint that indoles are apt to cause thermal self-polymerization at a high temperature.

For the purpose of improving the purity of recovered indoles, it is preferable to establish, prior to the distillation step, an additional step for the separation and removal of hydrocarbons contaminated as impurities into the extract.

Though separation of impurities may be effected by usually used means such as distillation, extraction, absorption, crystallization or the like, it is preferable to employ a method in which impurities contained in the extract are removed by extracting these impurities with the aforementioned organic solvent (B) from the viewpoint of easy handling and high impurities-removing efficiency.

Even when indoles are planned to be recovered from the foregoing extract by employing other means than the back extraction method with the organic solvent (A) or the distillation method, it is preferable to remove impurities from the extract using the organic solvent (B) prior to the recovery step.

In the aforementioned process of the present invention, the extraction step of indoles from an indoles-containing mixture as the starting material with formamide or a formamide-containing solution may preferably be carried out in the coexistence of the organic solvent (B). In this way, extractability and extraction selectivity of indoles with formamide or a formamide-containing solution are improved.

The organic solvent (B) may be added either to an indoles-containing mixture before the mixture is contacted with formamide or a formamide-containing solution, or to a mixture of the indoles-containing mixture with the formamide or formamide-containing solution during their contacting steps, for example during their mixing step or settling step after mixing. In other words, even during or after the mixing of the indoles-containing mixture with the formamide or formamide-containing solution, distribution equilibrium or partition coefficient between a raffinate layer and an extract layer changes and extraction selectivity of indoles increases by the addition of the organic solvent (B) provided that the solvent is added before the raffinate and extract layers start to separate from each other.

According to the present invention, formamide or a formamide-containing solution and various organic solvents used in the extraction process of indoles can be used repeatedly. That is, an indoles-free extract resulting from the recovery of indoles (formamide or a formamide-containing solution) can be used again as an extracting reagent for the extraction of indoles from a starting material (an indoles-containing mixture). In the same manner, the organic solvents (A) and (B) can also be used again by recovering and purifying them by distillation or the like means.

Compared to the case of usually used extraction process in which ethylene glycol or monoethanol amine is used as the extracting reagent, the process of the present invention for the extraction of indoles from an indoles-containing mixture making use of formamide as the extracting reagent has a slightly inferior extractability but significantly higher extraction selectivity. In addition, the use of formamide as the extracting reagent renders possible highly efficient extraction removal of impurities from an indoles-containing extract, by extracting with aliphatic hydrocarbons and/or alicyclic hydrocarbons. In consequence, purity of finally recovered indoles can be improved by the use of formamide as the extracting reagent, to a higher level of purity than the case of the use of ethylene glycol or monoethanolamine as the extracting reagent. Also, compared to the case of ethylene glycol and monoethanolamine, the use of formamide as the extracting reagent renders possible highly efficient recovery of indoles by extracting with ethers or the like from an indoles containing extract (also from an indoles-containing extract from which impurities are removed by extraction). On the basis of the above consideration, it is apparent that recovery of indoles can be achieved by the use of formamide as the extracting reagent more efficiently than the usually used means.

Since formamide hardly shows compatibility with any of aliphatic hydrocarbons, alicyclic hydrocarbons, ethers, aromatic hydrocarbons and halogenated hydrocarbons, losses of solvents during the steps for the extraction removal of impurities and extraction recovery of indoles are almost negligible.

Contrary to this, in the case of the usually used process for the extraction of indoles with ethylene glycol as an extracting reagent, thus extracted indoles are further extracted with diisopropyl ethers. In this instance, however, ethylene glycol partially dissolves in the ethers and, as the results, recovered indoles are contaminated by the ethylene glycol dissolved in the ethers. In the prior art process, therefore, it is necessary to remove ethylene glycol by washing or the like means in order to solve such a contamination problem, which inevitably results in the considerable loss of ethylene glycol and the necessity of establishing additional steps in the extraction process.

Examples of the process for the extraction of indoles according to the present invention are shown in FIGS. 1 and 2 as flow diagrams.

EXAMPLES

The following examples are provided to further illustrate the present invention but should not be regarded as limiting the invention.

EXAMPLE 1

A feed oil was prepared from a coal tar fraction boiling at 230° to 270° C. by removing acidic and basic components in the usual way. As shown in FIG. 1, to 10 ml of the feed oil was added 10 ml of formamide. After stirring vigorously for 30 minutes at 20° C., the resulting mixture was subjected to centrifugation to separate the mixture into a first extract (formamide solution) and a first raffinate. A 7 ml portion of the first extract was mixed with 7 ml of n heptane and the mixture was stirred vigorously for 30 minutes at 20° C. After settling for 10 minutes or longer, a second extract (n-heptane solution) thus separated from a second raffinate (formamide solution) was removed. As shown in FIG. 1, the thus obtained second raffinate was mixed with 7 ml of diisopropyl ether, and the mixture was stirred vigorously for 30 minutes at 20° C. and then settled for 10 minutes or longer to separate the mixture into a third extract (diisopropyl ether solution) and a third raffinate. Thereafter, diisopropyl ether was distilled off from the third extract by using a rotary evaporator to obtain a crude indole.

Components of the feed oil, the first, second and third extracts and the crude indole were analyzed by gas chromatography, with the results shown in Tables A and B. The feed oil contained 6500 ppm of sulfur.

Comparative Examples 1 and 2

The process of Example 1 was repeated except that formamide was replaced by ethylene glycol in Comparative Example 1 and that formamide was replaced by monoethanolamine in Comparative Example 2. The results are shown in Tables A and B.

TABLE A

Results of component analysis (units: wt %)

| | | First extract[1] | | |
|---|---|---|---|---|
| | Feed oil | Example 1 | Comparative Example 1 | Comparative Example 2 |
| Naphthalene | 13.4 | 11.2 | 13.7 | 16.4 |
| 2-Methylnaphthalene | 33.0 | 15.2 | 17.8 | 24.9 |
| 1-Methylnaphthalene | 13.0 | 6.1 | 7.4 | 10.1 |
| Diphenyl | 6.9 | 2.5 | 3.3 | 4.9 |
| Acenaphthene | 9.3 | 3.1 | 3.9 | 5.7 |
| Dibenzofuran | 5.2 | 2.4 | 3.0 | 4.4 |
| Fluorene | 2.1 | 0.7 | 0.9 | 1.4 |
| Indole | 3.6 | 52.6 | 43.2 | 23.4 |

[1] Composition of each extract excludes extracting reagent. That is, each composition shows contents of extracted components.

TABLE B

Results of extraction experiments

| | Example 1 | Comparative Example 1 | Comparative Example 2 |
|---|---|---|---|
| Indole extractability | | | |
| I (%) | 45.2 | 49.1 | 83.1 |
| II (%) | 4.5 | 4.3 | 0.9 |
| III (%) | 55.3 | 49.6 | 18.3 |
| Purity of crude indole (wt. %) | 88.0 | 67.8 | 31.4 |
| Concentration of sulphur contained in crude indole (ppm) | 480.0 | 1220.0 | 4390.0 |

(Note)

$$\text{Indole extractability I} = \frac{\text{weight of indole in the first extract}}{\text{weight of indole in feed oil}} \times 100 \, (\%)$$

$$\text{Indole extractability II} = \frac{\text{weight of indole in the second extract}}{\text{weight of indole in the first extract}} \times 100 \, (\%)$$

$$\text{Indole extractability III} = \frac{\text{weight of indole in the third extract}}{\text{weight of indole in the first extract}} \times 100 \, (\%)$$

Examples 2 and 3

A first extract obtained in the same manner as in Example 1 was extracted with the same volume of chloroform or benzene. Conditions for this extraction step were the same as those for the third extraction step with diisopropyl ether in Example 1. An extraction step equivalent to the second extraction with n-heptane in Example 1 was not applied to these examples.

The indole extractability (equivalent to the indole extractability III in Example 1) was 54.4% when chloroform was used and 54.9% in the case of benzene.

Example 4

The process of Example 1 was repeated except that cyclohexane was used instead of n-heptane.

The indole extractability II with cyclohexane was 7.3%, and the purity of recovered crude indole was 85.3 wt %.

Example 5

As shown in FIG. 2, to 10 ml of a stock oil prepared in the same manner as in Example 1 were added 10 ml of n-heptane and 10 ml of formamide. After vigorously stirring for 30 minutes at 20° C., the resulting mixture was settled for 30 minutes to separate the mixture into a first extract (formamide solution) and a first raffinate (n-heptane solution). Thereafter, as shown is FIG. 2, 7 ml of the first extract was treated in the same manner as in Example 1. Results of the component analysis are shown in Tables C and D.

TABLE C

Results of component analysis (units: wt %)

| | Feed oil | First extract[1] Example 5 |
|---|---|---|
| Naphthalene | 13.5 | 8.0 |
| 2-Methylnaphthalene | 34.1 | 14.3 |
| 1-Methylnaphthalene | 13.6 | 6.0 |
| Diphenyl | 7.1 | 2.8 |
| Acenaphthene | 9.2 | 3.2 |
| Dibenzofuran | 5.4 | 2.3 |
| Fluorene | 2.1 | 0.7 |
| Indole | 3.3 | 55.8 |

[1] Composition of each extract excludes extracting reagent. That is, each composition shows contents of extracted components.

TABLE D

Results of extraction experiments

| | Example 5 |
|---|---|
| Indole extractability I (%)[1] | 52.3 |
| Indole extractability II (%) | 4.6 |
| Indole extractability III (%) | 61.1 |
| Purity of crude indole (wt %) | 89.5 |

[1] Indole extractabilities I to III were calculated using the same formulae shown in the footnote of Table B.

As is evident from the results of Example 1, formamide has a low indole extractability (extraction capacity) but a high extraction selectivity compared to ethylene glycol and monoethanolamine. In addition, the use of formamide as an extracting reagent renders possible easy removal of impurities by their extraction with aliphatic hydrocarbons and, as the results, the purity of crude indole recovered is remarkably high, and the concentration of organic sulphuric compounds contained in crude indole is extremely low. Moreover, since extraction of indole with ethers can be achieved easily from a formamide extract, indole can be recovered with a small amount of extracting reagents (formamide and various organic solvents).

As the results of Examples 2 and 3 show, extraction of indole can be achieved efficiently from a formamide extract even with halogenated hydrocarbons or aromatic hydrocarbons. The results of Example 4 show that impurities as contaminants in a formamide extract can be removed efficiently by extraction with even alicyclic hydrocarbons. The purity of the crude indole recovered is remarkably high.

In addition, as is evident from the results of Example 5, extractability and extraction selectivity of indole with formamide increase when indole is extracted with formamide from a mixture of a stock oil and n-heptane, even if the content of indole in the starting material (feed oil+n-heptane) is low. That is, the indole content (w/v) in the starting material (feed oil+n-heptane) of Example 5 was less than half the value of the indole content (w/v) in the starting material (feed oil) of Example 1, but the extractability of indole with formamide (indole extractability I) was improved from 45.2% (Example 1) to 52.3% (Example 5) and the indole content in the first extract composition excluding the extracting reagent was improved from 52.6% (Example 1) to 55.8% (Example 5). Also in other words, the results of Example 5 show that extraction of indole with formamide can be achieved more efficiently and selectively when the extraction system is coexisted with aliphatic hydrocarbons or alicyclic hydrocarbons.

Thus, it is apparent that there has been provided, in accordance with the present invention, an industrially useful process for the extraction of indoles from indoles-containing mixture, in which a markedly high extraction selectivity of indoles was achieved by the use of formamide or a formamide-containing solution as the extracting reagent.

The advantages of the present invention are as follows:

(1) The extraction selectivity of indoles is high, and the removal of contained impurities is easy.

(2) Formamide (or formamide containing solution) and organic solvents are used in small quantity, almost without losses, and repeated use of these materials is possible, thus making it advantageous to reduce costs.

Therefore, the present invention proposes a preferable industrial process for the extraction of indoles.

While the present invention has been described in conjunction with specific embodiments thereof, it is evident that many alternatives, modifications and variations will be apparent to those skilled in the art in light of the foregoing description. Accordingly, it is intended to include all such alternatives, modifications and variations as set forth within the spirit and scope of the appended claim.

We claim:

1. A process for the extraction of indole comprising extracting an indole containing hydrocarbon mixture with formamide.

2. The process of claim 1 wherein the indole is recovered from the formamide extraction solution.

3. The process of claim 2 wherein the formamide extract is extracted with at least one organic solvent selected from the group consisting of aliphatic hydrocarbons and alicyclic hydrocarbons to remove impurities.

4. The process of claim 1 wherein the extraction is effected with a mixture of formamide and at least one organic solvent selected from the group consisting of aliphatic hydrocarbons and alicyclic hydrocarbons.

5. The process for the recovery of indole comprising extracting an indole containing hydrocarbon mixture with formamide and extracting the resulting solution with at least one organic solvent selected from the group consisting of ethers, aromatic hydrocarbons and halogenated hydrocarbons.

6. The process for extracting indole of claim 5 wherein a purification step is interposed between said two extracting steps, said purification step comprising extracting impurities from the extract resulting from extracting an indole containing mixture wtih a mixture of formamide and at least one organic solvent selected from the group consisting of aliphatic hydrocarbons and alicyclic hydrocarbons.

* * * * *